United States Patent [19]
Falb et al.

[11] Patent Number: 5,928,411
[45] Date of Patent: Jul. 27, 1999

[54] DEVICE FOR ABSORBING A GAS MIXTURE CONSISTING OF LAUGHING GAS AND ANESTHETIC VAPOR

[75] Inventors: Wolfgang Falb, Krummesse; Karl-Ludwig Gippert, Lübeck; Uwe Bausch, Lübeck; Dirk Stefan Reichert, Lübeck; Stefan Linke, Lübeck; Udo Feldhoff, Malkendorf, all of Germany

[73] Assignee: Drägerwerk AG, Lübeck, Germany

[21] Appl. No.: 08/897,716

[22] Filed: Jul. 21, 1997

[30] Foreign Application Priority Data

Feb. 21, 1997 [DE] Germany ............ 197 06 806

[51] Int. Cl.$^6$ ................................ B01D 53/04
[52] U.S. Cl. ................ 95/129; 95/131; 95/132; 95/142; 95/902
[58] Field of Search ................ 95/128, 129, 131, 95/132, 142, 902; 96/121, 130–132, 143

[56] References Cited

U.S. PATENT DOCUMENTS

| | | | |
|---|---|---|---|
| 2,930,445 | 3/1960 | Glass et al. | 96/131 |
| 3,140,934 | 7/1964 | Mandell, Jr. et al. | 95/132 |
| 3,489,507 | 1/1970 | Gardner et al. | 95/128 X |
| 3,689,212 | 9/1972 | Petit et al. | 95/128 X |
| 3,961,919 | 6/1976 | Lamoreaux | 96/132 |
| 4,153,429 | 5/1979 | Matthews et al. | 95/129 X |
| 4,507,271 | 3/1985 | Van Deyck et al. | 95/129 X |
| 4,552,570 | 11/1985 | Gravatt | 96/130 X |
| 4,636,225 | 1/1987 | Klein et al. | 96/132 X |
| 4,983,190 | 1/1991 | Verrando et al. | 96/130 X |
| 5,261,948 | 11/1993 | Fdey et al. | 95/142 |
| 5,376,164 | 12/1994 | Zarchy et al. | 95/132 X |
| 5,417,950 | 5/1995 | Sheu et al. | 95/128 X |
| 5,425,240 | 6/1995 | Jain et al. | 96/130 X |
| 5,514,204 | 5/1996 | Sheu et al. | 95/129 X |
| 5,670,125 | 9/1997 | Sheu et al. | 95/129 X |

FOREIGN PATENT DOCUMENTS

| | | | |
|---|---|---|---|
| 0 113 023 | 11/1983 | European Pat. Off. | |
| 3244370 | 6/1984 | Germany | 95/129 |
| 42 08 521 A1 | 9/1993 | Germany | |
| 4308940 | 9/1994 | Germany | 95/142 |
| 56-021624 | 2/1981 | Japan | 96/131 |
| 56-076223 | 6/1981 | Japan | 95/128 |
| 2124103 | 2/1984 | United Kingdom | 95/129 |

*Primary Examiner*—Robert Spitzer
*Attorney, Agent, or Firm*—McGlew and Tuttle

[57] ABSTRACT

A device for removing at least laughing gas and anesthetic vapor from a gas sample based on a molecular sieve shall be improved such that it possesses good adsorption properties for both gas components. A molecular sieve arrangement is provided, which is flown through from a gas inlet to a gas outlet and comprises a first molecular sieve area with a first pore size between about 0.3 nm and 0.5 nm and a second molecular sieve area with a second pore size between about 0.8 nm and 1 nm.

5 Claims, 2 Drawing Sheets

DEVICE FOR ABSORBING A GAS MIXTURE CONSISTING OF LAUGHING GAS AND ANESTHETIC VAPOR

FIELD OF THE INVENTION

The present invention pertains to a device for removing at least laughing gas and anesthetic vapor from a gas sample.

BACKGROUND OF THE INVENTION

A laughing gas-oxygen mixture, to which a defined amount of anesthetic is added in the form of a vapor, is used in many cases in the field of inhalation anesthesia. Since prior-art anesthetic respirators operate, in general, in the so-called excess gas mode, in which more gaseous anesthetic is fed into the respiratory circuit than is consumed by the patient, a certain volume of gas must be removed and disposed of via a central gaseous anesthetic exhaust unit during the use of the apparatus. An activated carbon filter is provided as the adsorbent for anesthetic vapor in a gaseous anesthetic processing unit known from DE 42 08 521 A1, and the laughing gas is decomposed into oxygen and nitrogen in a catalyst cartridge, because it is not bound by the activated carbon filter. This method of processing gaseous anesthetics is relatively expensive, because at least two purification steps are necessary.

It has been known from EP 113 023 B1 that laughing gas can be removed from a hydrogen-nitrogen monoxide gas mixture with a molecular sieve having a pore size between 0.4 and 1 nm.

However, the removal of two components from a gas mixture, laughing gas and anesthetic vapor in this case, is possible only insufficiently with the prior-art molecular sieve, because only one of the components is always adsorbed sufficiently, depending on the pore size.

SUMMARY AND OBJECTS OF THE INVENTION

The primary object of the present invention is to provide an adsorbent for a mixture of laughing gas and anesthetic vapor based on a molecular sieve that possesses good adsorption properties for both gas components.

According to the invention, a device is provided for removing at least laughing gas and anesthetic vapor from a gas sample. The device includes a molecular sieve arrangement formed of a mixture of molecular sieves with a first pore sires between 0.3 nm and 0.5 nm and a second pore sizes between about 0.8 nm and 1 nm.

The advantage of the present invention is essentially that the separation performance is markedly improved by the use of a molecular sieve with different adsorption ranges designed for the components to be removed. A molecular sieve arrangement consisting of a molecular sieve mixture with first pore sizes between 0.3 nm and 0.5 nm and second pore sizes between 0.8 nm and 1 nm is especially suitable for the adsorption of a gas mixture consisting of anesthetic vapor and laughing gas.

The molecular sieve according to the present invention may be used especially advantageously at the excess gas outlet of an inhalation anesthesia apparatus to remove laughing gas and anesthetic vapor. Another advantageous application of the molecular sieve according to the present invention is on components of the anesthesia apparatus through which the anesthetic gas flows and from which anesthetic gas escapes during brief periods of time, e.g., during changeover processes. For example, the anesthetic gas can be eliminated immediately at the point at which such gas escapes from a changeover switch by means of a molecular sieve of a cartridge-like design, which is then replaced by the service provider at predetermined time intervals.

One exemplary embodiment of the present invention is shown in the drawings and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
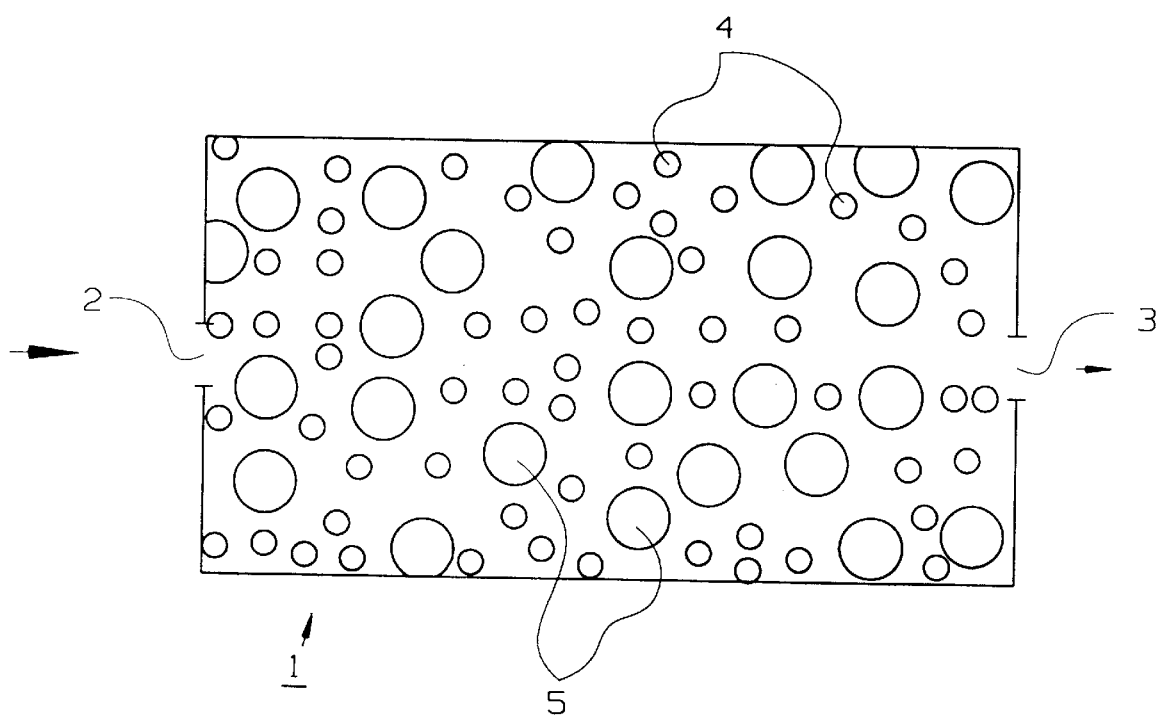
FIG. 1 is a first molecular sieve arrangement.

FIG. 1 shows schematically a first molecular sieve arrangement 1, through which medium flows from a gas inlet 2 to a gas outlet 3. The first molecular sieve arrangement 1 comprises a molecular sieve mixture with a first pore size 4 between 0.3 nm and 0.5 nm and a second pore size 5 between 0.8 nm and 1 nm.

The different pore sizes 4, 5 are illustrated in FIG. 1 by circles with larger and smaller radii.

Figure 2:
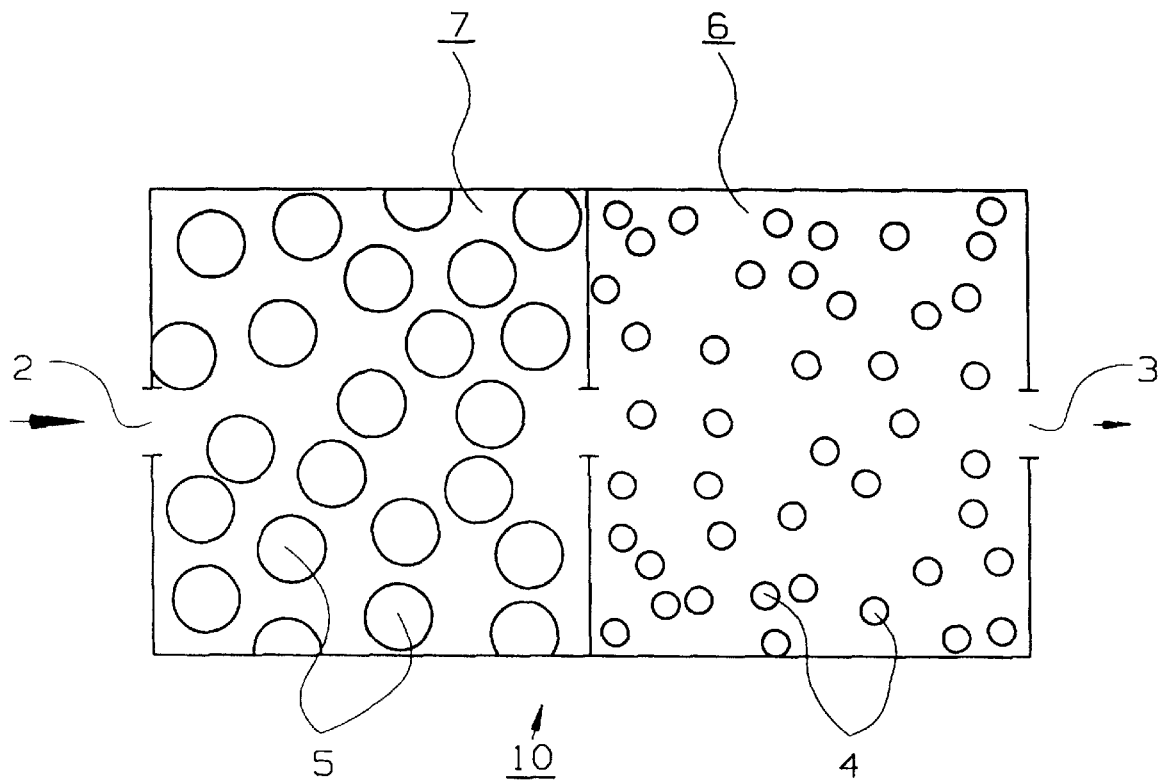
FIG. 2 is a second molecular sieve arrangement.

FIG. 2 shows schematically a second molecular sieve arrangement 10. Identical components are designated with the same reference numbers as in FIG. 1. What is different from FIG. 1 is that molecular sieve components with the first pore size 4 are integrated in a first molecular sieve area 6 and molecular sieve components with the second pore size 5 are integrated in a second molecular sieve area 7. The flow through the second molecular sieve arrangement 10 is in the direction from the second area 7 into the first area 6. A molecular sieve structure thus stratified offers the advantage that a high degree of purity is obtained at the gas outlet 3.

The present invention shall be illustrated on the basis of an example:

Six g a of molecular sieve mixture, e.g., a mixture arrangement purchased from the firm of Merck, Darmstadt, having a pore size of 1 nm and 0.5 nm, were charged with about 10,000 ppm of halothane and about 10,000 ppm of laughing gas (corresponding to about 200 mg of halothane and about 200 mL of gaseous laughing gas). The charge of the molecular sieve was about 19 mL of gaseous halothane (corresponding to 50%) and 5 mL (corresponding to 14%) of laughing gas per g of molecular sieve. The regeneration of the molecular sieve was performed by heating for 4 hours at 120° C.

While a specific embodiment of the invention has been shown and described in detail to illustrate the application of the principles of the invention, it will be understood that the invention may be embodied otherwise without departing from such principles.

What is claimed is:

1. A method for removing at least laughing gas and anesthetic vapor from a gas sample, comprising:

providing an inhalation anesthesia apparatus with an excess gas outlet;

providing a device as a component of the anesthesia apparatus attached to said excess gas outlet, the device having a molecular sieve arrangement including
- a first molecular sieve component with pores of sizes between about 0.3 nm and 0.5 nm and
- a second molecular sieve component with pores of sizes between about 0.8 nm and 1 nm; and absorbing laughing gas and anesthetic vapor as the gas mixture passes through said device.

2. The method in accordance with claim 1, wherein said first molecular sieve component is provided in a first molecular sieve space, and said second molecular sieve component is provided in a second molecular sieve space.

3. The device in accordance with claim 1, wherein said first molecular sieve component is integrated with said second molecular sieve component in a single molecular sieve space.

4. The method in accordance with claim 1, wherein said device is a cartridge and is replaced by a substantially identical device at predetermined time intervals.

5. The device in accordance with claim 4, wherein said first molecular sieve and said second molecular sieve are regenerated.

* * * * *